(12) United States Patent
Schaffhausen

(10) Patent No.: US 7,608,092 B1
(45) Date of Patent: Oct. 27, 2009

(54) METHOD AND APPARATUS FOR PERFORMING MENISCUS REPAIR

(75) Inventor: Cory Schaffhausen, Palo Alto, CA (US)

(73) Assignee: Biomet Sports Medicince, LLC, Warsaw, IN (US)

( * ) Notice: Subject to any disclaimer, the term of this patent is extended or adjusted under 35 U.S.C. 154(b) by 342 days.

(21) Appl. No.: 10/784,031

(22) Filed: Feb. 20, 2004

(51) Int. Cl.
*A61B 17/04* (2006.01)

(52) U.S. Cl. ...................................... 606/232

(58) Field of Classification Search ............... 606/232, 606/144–150, 213, 233
See application file for complete search history.

(56) References Cited

U.S. PATENT DOCUMENTS

| | | |
|---|---|---|
| 26,501 A | 10/1859 | Kendrick et al. |
| 65,499 A | 6/1867 | Miller |
| 126,366 A | 4/1872 | Wills |
| 233,475 A | 10/1880 | Cook et al. |
| 261,501 A | 7/1882 | Vandermark |
| 401,677 A | 11/1889 | Roeder |
| 417,805 A | 12/1889 | Beaman |
| 487,304 A | 12/1892 | Todd |
| 762,710 A | 6/1904 | Hall |
| 837,767 A | 12/1906 | Aims |
| 838,203 A | 12/1906 | Neil |
| 1,059,631 A | 4/1913 | Popovics |
| 1,131,155 A | 9/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |

(Continued)

FOREIGN PATENT DOCUMENTS

AU 49572/64 3/1966

(Continued)

OTHER PUBLICATIONS

F. Alan Barber, M.D., "Using Sutures and Anchors," San Diego Shoulder Arthroscopy Course, 17th Annual Meeting.

(Continued)

*Primary Examiner*—Todd E Manahan
*Assistant Examiner*—Lindsey Bachman
(74) *Attorney, Agent, or Firm*—Harness, Dickey

(57) ABSTRACT

An apparatus and method of repairing a tear in body tissue includes inserting a needle containing a retaining head from a first insertion position on a first outer surface of the body tissue, through the tear and to a second outer surface of the body tissue. The retaining head is ejected from the insertion needle and grasps the second outer surface in an engaged position. An anchor coupled to the retaining head by a flexible member is advanced from a second insertion position on the first outer surface of the body tissue to a position at least through a portion of the tear. The flexible member extends a distance along the first outer surface of the body tissue from the first insertion position to the second insertion position.

23 Claims, 4 Drawing Sheets

U.S. PATENT DOCUMENTS

| | | |
|---|---|---|
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,312,337 A | 1/1982 | Donohue |
| 4,316,469 A | 2/1982 | Kapitanov |
| 4,326,531 A | 4/1982 | Shimonaka |

| | | | | | |
|---|---|---|---|---|---|
| 4,345,601 A | 8/1982 | Fukuda | 4,773,910 A | 9/1988 | Chen et al. |
| 4,349,027 A | 9/1982 | DiFrancesco | 4,775,380 A | 10/1988 | Seedhom et al. |
| 4,388,921 A | 6/1983 | Sutter et al. | 4,776,328 A | 10/1988 | Frey et al. |
| 4,400,833 A | 8/1983 | Kurland | 4,781,190 A | 11/1988 | Lee |
| 4,402,445 A | 9/1983 | Green | 4,784,126 A | 11/1988 | Hourahane |
| 4,409,974 A | 10/1983 | Freedland | 4,787,882 A | 11/1988 | Claren et al. |
| 4,438,769 A | 3/1984 | Pratt et al. | 4,790,297 A | 12/1988 | Luque et al. |
| 4,441,489 A | 4/1984 | Evans et al. | 4,809,695 A | 3/1989 | Gwathmey et al. |
| 4,454,875 A | 6/1984 | Pratt et al. | 4,813,406 A | 3/1989 | Ogle, II |
| 4,462,395 A | 7/1984 | Johnson | 4,823,794 A | 4/1989 | Pierce |
| 4,463,753 A | 8/1984 | Gustilo | 4,828,562 A | 5/1989 | Kenna |
| 4,473,102 A | 9/1984 | Ohman et al. | 4,832,026 A | 5/1989 | Jones |
| 4,484,570 A | 11/1984 | Sutter et al. | 4,834,098 A | 5/1989 | Jones |
| 4,493,323 A * | 1/1985 | Albright et al. ............ 606/144 | 4,841,960 A | 6/1989 | Garner |
| 4,496,468 A | 1/1985 | House et al. | 4,851,005 A | 7/1989 | Hunt et al. |
| 4,505,274 A | 3/1985 | Speelman | 4,858,608 A | 8/1989 | McQuilkin |
| 4,509,516 A | 4/1985 | Richmond | 4,860,513 A | 8/1989 | Whitman |
| 4,531,522 A | 7/1985 | Bedi et al. | 4,863,383 A | 9/1989 | Grafelmann et al. |
| 4,532,926 A | 8/1985 | O'Holla | 4,870,957 A | 10/1989 | Goble et al. |
| 4,534,350 A | 8/1985 | Golden et al. | 4,873,976 A | 10/1989 | Schreiber |
| 4,535,764 A | 8/1985 | Ebert | 4,887,601 A | 12/1989 | Richards |
| 4,537,185 A | 8/1985 | Stednitz | 4,890,615 A | 1/1990 | Caspari et al. |
| 4,549,652 A | 10/1985 | Free | 4,893,619 A | 1/1990 | Dale et al. |
| 4,561,432 A | 12/1985 | Mazor | 4,893,974 A | 1/1990 | Fischer et al. |
| 4,564,007 A | 1/1986 | Coombs et al. | 4,895,148 A | 1/1990 | Bays et al. |
| 4,570,623 A | 2/1986 | Ellison et al. | 4,896,668 A | 1/1990 | Popoff et al. |
| 4,573,844 A | 3/1986 | Smith | 4,898,156 A | 2/1990 | Gatturna et al. |
| 4,576,608 A | 3/1986 | Homsy | 4,899,743 A | 2/1990 | Nicholson et al. |
| 4,584,722 A | 4/1986 | Levy et al. | 4,901,721 A | 2/1990 | Hakki |
| 4,590,928 A | 5/1986 | Hunt et al. | 4,923,461 A | 5/1990 | Caspari et al. |
| 4,595,007 A | 6/1986 | Mericle | 4,927,421 A | 5/1990 | Goble et al. |
| 4,596,249 A | 6/1986 | Freda et al. | 4,946,468 A | 8/1990 | Li |
| 4,602,635 A | 7/1986 | Mulhollan et al. | 4,950,270 A | 8/1990 | Bowman et al. |
| 4,602,636 A | 7/1986 | Noiles | 4,950,285 A | 8/1990 | Wilk |
| 4,604,997 A | 8/1986 | De Bastiani et al. | 4,960,381 A | 10/1990 | Niznick |
| 4,605,414 A | 8/1986 | Czajka | 4,961,741 A | 10/1990 | Hayhurst |
| 4,616,650 A | 10/1986 | Green et al. | 4,968,315 A | 11/1990 | Gatturna |
| 4,621,640 A | 11/1986 | Mulhollan et al. | 4,968,317 A | 11/1990 | Tormala et al. |
| 4,624,254 A | 11/1986 | McGarry et al. | 4,969,886 A | 11/1990 | Cziffer et al. |
| 4,632,100 A | 12/1986 | Somers et al. | 4,976,736 A | 12/1990 | White et al. |
| 4,635,637 A | 1/1987 | Schreiber | 4,978,350 A | 12/1990 | Wagenknecht et al. |
| 4,636,121 A | 1/1987 | Miller | 4,979,956 A | 12/1990 | Silvestrini |
| 4,641,652 A | 2/1987 | Hutterer et al. | 4,983,176 A | 1/1991 | Cushman et al. |
| 4,649,952 A | 3/1987 | Jobe | 4,988,351 A | 1/1991 | Paulos et al. |
| 4,653,486 A | 3/1987 | Coker | 4,997,433 A | 3/1991 | Goble et al. |
| 4,653,487 A | 3/1987 | Maale | 5,002,550 A | 3/1991 | Li |
| 4,653,489 A | 3/1987 | Tronzo | 5,002,562 A | 3/1991 | Oberlander |
| 4,655,777 A | 4/1987 | Dunn et al. | 5,007,921 A | 4/1991 | Brown |
| 4,662,068 A | 5/1987 | Polonsky | 5,030,224 A | 7/1991 | Wright et al. |
| 4,667,662 A | 5/1987 | Titone et al. | 5,037,422 A | 8/1991 | Hayhurst et al. |
| 4,667,675 A | 5/1987 | Davis | 5,041,129 A | 8/1991 | Hayhurst et al. |
| 4,669,473 A * | 6/1987 | Richards et al. ............ 606/215 | 5,046,513 A | 9/1991 | Gatturna et al. |
| 4,683,895 A | 8/1987 | Pohndorf | 5,047,030 A | 9/1991 | Draenert et al. |
| 4,688,561 A | 8/1987 | Reese | 5,053,046 A | 10/1991 | Janese |
| 4,690,169 A | 9/1987 | Jobe | 5,053,047 A | 10/1991 | Yoon |
| 4,705,040 A | 11/1987 | Mueller et al. | 5,059,201 A | 10/1991 | Asnis |
| 4,708,132 A | 11/1987 | Silvestrini | 5,059,206 A | 10/1991 | Winters |
| 4,716,893 A | 1/1988 | Fischer et al. | 5,062,344 A | 11/1991 | Gerker |
| 4,719,671 A | 1/1988 | Ito et al. | 5,062,843 A | 11/1991 | Mahony, III |
| 4,719,917 A | 1/1988 | Barrows et al. | 5,078,731 A | 1/1992 | Hayhurst |
| 4,723,540 A | 2/1988 | Gilmer, Jr. | 5,078,843 A | 1/1992 | Pratt |
| 4,724,839 A | 2/1988 | Bedi et al. | 5,084,050 A | 1/1992 | Draenert |
| 4,728,332 A | 3/1988 | Albrektsson et al. | 5,084,058 A | 1/1992 | Li |
| 4,738,255 A | 4/1988 | Goble et al. | 5,085,661 A | 2/1992 | Moss |
| 4,741,330 A | 5/1988 | Hayhurst | 5,087,263 A | 2/1992 | Li |
| 4,741,336 A | 5/1988 | Failla et al. | 5,092,866 A | 3/1992 | Breard et al. |
| 4,744,353 A | 5/1988 | McFarland | 5,098,435 A | 3/1992 | Stednitz et al. |
| 4,744,793 A | 5/1988 | Parr et al. | 5,100,415 A | 3/1992 | Hayhurst |
| 4,750,492 A | 6/1988 | Jacobs | 5,100,417 A | 3/1992 | Cerier et al. |
| 4,760,843 A | 8/1988 | Fischer et al. | 5,116,337 A | 5/1992 | Johnson |
| 4,760,848 A | 8/1988 | Hasson | 5,116,373 A | 5/1992 | Jakob et al. |
| 4,772,261 A | 9/1988 | Von Hoff et al. | 5,116,375 A | 5/1992 | Hofmann |
| 4,772,286 A | 9/1988 | Goble et al. | 5,123,913 A | 6/1992 | Wilk et al. |

| | | | | | | |
|---|---|---|---|---|---|---|
| 5,127,785 A | 7/1992 | Faucher et al. | 5,370,661 A | 12/1994 | Branch | |
| 5,129,901 A | 7/1992 | Decoste | 5,370,662 A | 12/1994 | Stone et al. | |
| 5,129,902 A | 7/1992 | Goble et al. | 5,372,146 A | 12/1994 | Branch | |
| 5,129,904 A | 7/1992 | Illi et al. | 5,372,604 A | 12/1994 | Trott | |
| 5,129,906 A | 7/1992 | Ross et al. | 5,372,821 A | 12/1994 | Badylak et al. | |
| 5,139,499 A | 8/1992 | Small et al. | 5,374,268 A | 12/1994 | Sander | |
| 5,139,520 A | 8/1992 | Rosenberg | 5,379,492 A | 1/1995 | Glesser | |
| 5,143,498 A | 9/1992 | Whitman | 5,383,878 A | 1/1995 | Roger et al. | |
| 5,147,362 A | 9/1992 | Goble | 5,391,171 A | 2/1995 | Schmieding | |
| 5,149,329 A | 9/1992 | Richardson | 5,391,176 A | 2/1995 | de la Torre | |
| 5,152,790 A | 10/1992 | Rosenberg et al. | 5,393,302 A | 2/1995 | Clark et al. | |
| 5,154,189 A | 10/1992 | Oberlander | RE34,871 E | 3/1995 | McGuire et al. | |
| 5,156,616 A | 10/1992 | Meadows et al. | 5,397,356 A | 3/1995 | Goble et al. | |
| 5,163,960 A | 11/1992 | Bonutti | 5,403,328 A | 4/1995 | Shallman | |
| D331,626 S | 12/1992 | Hayhurst et al. | 5,403,329 A | 4/1995 | Hinchcliffe | |
| 5,169,400 A | 12/1992 | Muhling et al. | 5,403,348 A | 4/1995 | Bonutti | |
| 5,176,682 A | 1/1993 | Chow | 5,417,691 A | 5/1995 | Hayhurst | |
| 5,178,629 A | 1/1993 | Kammerer | 5,417,712 A | 5/1995 | Whittaker et al. | |
| 5,183,458 A | 2/1993 | Marx | 5,423,819 A | 6/1995 | Small et al. | |
| 5,192,282 A | 3/1993 | Draenert et al. | 5,423,823 A | 6/1995 | Schmieding | |
| 5,197,987 A | 3/1993 | Koch et al. | 5,423,860 A | 6/1995 | Lizardi et al. | |
| 5,203,784 A | 4/1993 | Ross et al. | 5,425,733 A | 6/1995 | Schmieding | |
| 5,203,787 A | 4/1993 | Noblitt et al. | 5,425,766 A | 6/1995 | Bowald et al. | |
| 5,207,679 A | 5/1993 | Li | 5,433,751 A | 7/1995 | Christel et al. | |
| 5,209,753 A | 5/1993 | Biedermann et al. | 5,437,680 A | 8/1995 | Yoon | |
| 5,209,805 A | 5/1993 | Spraggins | 5,439,684 A | 8/1995 | Prewett et al. | |
| 5,211,647 A | 5/1993 | Schmieding | 5,443,468 A | 8/1995 | Johnson | |
| 5,211,650 A | 5/1993 | Noda | 5,443,482 A | 8/1995 | Stone et al. | |
| 5,214,987 A | 6/1993 | Fenton, Sr. | 5,443,483 A | 8/1995 | Kirsch et al. | |
| 5,219,359 A | 6/1993 | McQuilkin et al. | 5,443,509 A | 8/1995 | Boucher et al. | |
| 5,224,946 A | 7/1993 | Hayhurst et al. | 5,445,833 A | 8/1995 | Badylak et al. | |
| 5,230,699 A | 7/1993 | Grasinger | 5,447,512 A | 9/1995 | Wilson et al. | |
| 5,232,436 A | 8/1993 | Janevski | 5,451,203 A | 9/1995 | Lamb | |
| 5,234,435 A | 8/1993 | Seagrave, Jr. | 5,454,811 A | 10/1995 | Huebner | |
| 5,236,445 A | 8/1993 | Hayhurst et al. | 5,456,685 A | 10/1995 | Huebner | |
| 5,236,461 A | 8/1993 | Forte | 5,456,722 A | 10/1995 | McLeod et al. | |
| 5,242,447 A | 9/1993 | Borzone | 5,458,601 A | 10/1995 | Young, Jr. et al. | |
| 5,246,441 A | 9/1993 | Ross et al. | 5,458,604 A | 10/1995 | Schmieding | |
| 5,249,899 A | 10/1993 | Wilson | 5,462,560 A * | 10/1995 | Stevens | 606/144 |
| 5,258,015 A | 11/1993 | Li et al. | 5,464,426 A | 11/1995 | Bonutti | |
| 5,258,016 A | 11/1993 | DiPoto et al. | 5,464,427 A | 11/1995 | Curtis et al. | |
| 5,258,040 A | 11/1993 | Bruchman et al. | 5,464,440 A | 11/1995 | Johansson et al. | |
| 5,268,001 A | 12/1993 | Nicholson et al. | 5,466,237 A | 11/1995 | Byrd, III et al. | |
| 5,269,160 A | 12/1993 | Wood | 5,467,786 A * | 11/1995 | Allen et al. | 128/898 |
| 5,269,783 A | 12/1993 | Sander | 5,470,334 A | 11/1995 | Ross et al. | |
| 5,269,809 A | 12/1993 | Hayhurst et al. | 5,470,337 A | 11/1995 | Moss | |
| 5,281,422 A | 1/1994 | Badylak et al. | 5,470,338 A | 11/1995 | Whitfield et al. | |
| 5,282,809 A | 2/1994 | Kammerer et al. | 5,472,452 A | 12/1995 | Trott | |
| 5,282,832 A | 2/1994 | Toso et al. | 5,474,565 A | 12/1995 | Trott | |
| 5,285,040 A | 2/1994 | Brandberg et al. | 5,474,568 A | 12/1995 | Scott | |
| 5,290,217 A | 3/1994 | Campos | 5,474,572 A | 12/1995 | Hayhurst | |
| 5,306,301 A | 4/1994 | Graf et al. | 5,478,344 A | 12/1995 | Stone et al. | |
| 5,312,422 A | 5/1994 | Trott | 5,478,345 A | 12/1995 | Stone et al. | |
| 5,312,438 A | 5/1994 | Johnson | 5,480,403 A | 1/1996 | Lee et al. | |
| 5,318,577 A | 6/1994 | Li | 5,480,406 A | 1/1996 | Nolan et al. | |
| 5,318,578 A | 6/1994 | Hasson | 5,484,442 A | 1/1996 | Melker et al. | |
| 5,320,115 A | 6/1994 | Kenna | 5,486,197 A | 1/1996 | Le et al. | |
| 5,320,626 A | 6/1994 | Schmieding | 5,490,750 A | 2/1996 | Gundy | |
| 5,320,633 A | 6/1994 | Allen et al. | 5,496,331 A | 3/1996 | Xu et al. | |
| 5,324,308 A | 6/1994 | Pierce | 5,496,348 A | 3/1996 | Bonutti | |
| 5,334,204 A | 8/1994 | Clewett et al. | 5,500,000 A | 3/1996 | Feagin et al. | |
| 5,336,229 A | 8/1994 | Noda | 5,505,736 A | 4/1996 | Reimels et al. | |
| 5,336,231 A | 8/1994 | Adair | 5,507,754 A | 4/1996 | Green et al. | |
| 5,336,240 A | 8/1994 | Metzler et al. | 5,520,691 A | 5/1996 | Branch | |
| 5,342,369 A | 8/1994 | Harryman, II | 5,520,702 A | 5/1996 | Sauer et al. | |
| 5,346,462 A | 9/1994 | Barber | 5,522,817 A | 6/1996 | Sander et al. | |
| 5,354,298 A | 10/1994 | Lee et al. | 5,522,820 A | 6/1996 | Caspari et al. | |
| 5,356,413 A | 10/1994 | Martins et al. | 5,522,844 A | 6/1996 | Johnson | |
| 5,358,511 A | 10/1994 | Gatturna et al. | 5,522,845 A | 6/1996 | Wenstrom, Jr. | |
| 5,360,431 A | 11/1994 | Puno et al. | 5,522,846 A | 6/1996 | Bonutti | |
| 5,362,294 A | 11/1994 | Seitzinger | 5,524,946 A | 6/1996 | Thompson | |
| 5,364,400 A | 11/1994 | Rego, Jr. et al. | 5,527,321 A | 6/1996 | Hinchliffe | |
| 5,368,599 A | 11/1994 | Hirsch et al. | 5,527,342 A | 6/1996 | Pietrzak et al. | |

| Patent | Date | Inventor |
|---|---|---|
| 5,527,343 A | 6/1996 | Bonutti |
| 5,534,012 A | 7/1996 | Bonutti |
| 5,540,718 A | 7/1996 | Bartlett |
| 5,545,178 A | 8/1996 | Kensey et al. |
| 5,545,228 A | 8/1996 | Kambin |
| 5,549,613 A | 8/1996 | Goble et al. |
| 5,549,617 A | 8/1996 | Green et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,548 A | 11/1996 | Nazre et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,422 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,352 A | 10/1997 | Clancy, III et al. |
| 5,683,419 A | 11/1997 | Thal |
| 5,688,285 A | 11/1997 | Yamada et al. |
| 5,690,676 A | 11/1997 | DiPoto et al. |
| 5,690,678 A | 11/1997 | Johnson |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A * | 12/1997 | Oberlander .................. 128/898 |
| 5,707,373 A | 1/1998 | Sevrain et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Oijma et al. |
| 5,718,717 A | 2/1998 | Bonutti |
| 5,720,765 A | 2/1998 | Thal |
| 5,720,766 A | 2/1998 | Zang et al. |
| 5,725,549 A | 3/1998 | Lam |
| 5,725,556 A | 3/1998 | Moser et al. |
| 5,725,581 A | 3/1998 | Brånemark et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,766,176 A | 6/1998 | Duncan |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,860,973 A | 1/1999 | Michelson |
| 5,868,740 A | 2/1999 | LeVeen et al. |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |

| | | | | | |
|---|---|---|---|---|---|
| 5,921,986 A | 7/1999 | Bonutti | 6,139,565 A | 10/2000 | Stone et al. |
| 5,925,008 A | 7/1999 | Douglas | RE36,974 E | 11/2000 | Bonutti |
| 5,928,267 A | 7/1999 | Bonutti et al. | 6,143,017 A | 11/2000 | Thal |
| 5,931,838 A | 8/1999 | Vito | 6,146,406 A | 11/2000 | Shluzas et al. |
| 5,931,844 A | 8/1999 | Thompson et al. | 6,146,408 A | 11/2000 | Bartlett |
| 5,931,869 A | 8/1999 | Boucher et al. | 6,149,653 A | 11/2000 | Deslauriers |
| 5,935,149 A | 8/1999 | Ek | 6,149,669 A | 11/2000 | Li |
| 5,938,668 A | 8/1999 | Scirica et al. | 6,152,928 A | 11/2000 | Wenstrom, Jr. |
| 5,941,439 A | 8/1999 | Kammerer et al. | 6,152,934 A | 11/2000 | Harper et al. |
| 5,941,900 A | 8/1999 | Bonutti | 6,152,936 A | 11/2000 | Christy et al. |
| 5,944,739 A | 8/1999 | Zlock et al. | 6,152,949 A | 11/2000 | Bonutti |
| 5,947,915 A | 9/1999 | Thibodo, Jr. | 6,156,039 A | 12/2000 | Thal |
| 5,947,982 A | 9/1999 | Duran | 6,156,056 A | 12/2000 | Kearns et al. |
| 5,948,002 A | 9/1999 | Bonutti | 6,159,234 A | 12/2000 | Bonutti et al. |
| 5,951,559 A | 9/1999 | Burkhart | 6,165,203 A | 12/2000 | Krebs |
| 5,951,560 A | 9/1999 | Simon et al. | 6,168,598 B1 | 1/2001 | Martello |
| 5,954,747 A * | 9/1999 | Clark .................. 606/216 | 6,168,628 B1 | 1/2001 | Huebner |
| 5,957,953 A | 9/1999 | DiPoto et al. | 6,187,025 B1 | 2/2001 | Machek |
| 5,961,521 A | 10/1999 | Roger et al. | 6,190,401 B1 | 2/2001 | Green et al. |
| 5,961,524 A | 10/1999 | Crombie | 6,190,411 B1 | 2/2001 | Lo et al. |
| 5,964,764 A | 10/1999 | West, Jr. et al. | 6,193,754 B1 | 2/2001 | Seedhom et al. |
| 5,964,767 A | 10/1999 | Tapia et al. | 6,200,329 B1 | 3/2001 | Fung et al. |
| 5,964,783 A | 10/1999 | Grafton et al. | 6,200,330 B1 | 3/2001 | Benderev et al. |
| 5,968,045 A | 10/1999 | Frazier | 6,203,565 B1 | 3/2001 | Bonutti et al. |
| 5,968,047 A | 10/1999 | Reed | 6,203,572 B1 | 3/2001 | Johnson et al. |
| 5,976,125 A | 11/1999 | Graham | 6,206,883 B1 | 3/2001 | Tunc |
| 5,976,127 A | 11/1999 | Lax | 6,210,376 B1 | 4/2001 | Grayson |
| 5,980,524 A | 11/1999 | Justin et al. | 6,214,012 B1 | 4/2001 | Karpman et al. |
| 5,980,558 A | 11/1999 | Wiley | 6,221,107 B1 | 4/2001 | Steiner et al. |
| 5,980,559 A | 11/1999 | Bonutti | 6,228,096 B1 | 5/2001 | Marchand |
| 5,989,252 A | 11/1999 | Fumex | 6,231,592 B1 | 5/2001 | Bonutti et al. |
| 5,989,256 A | 11/1999 | Kuslich et al. | 6,235,057 B1 | 5/2001 | Roger et al. |
| 5,989,282 A | 11/1999 | Bonutti | 6,238,395 B1 | 5/2001 | Bonutti |
| 5,993,452 A | 11/1999 | Vandewalle | 6,241,747 B1 | 6/2001 | Ruff |
| 5,997,542 A | 12/1999 | Burke | 6,241,771 B1 | 6/2001 | Gresser et al. |
| 5,997,552 A | 12/1999 | Person et al. | 6,245,081 B1 | 6/2001 | Bowman et al. |
| 6,001,100 A | 12/1999 | Sherman et al. | 6,258,091 B1 | 7/2001 | Sevrain et al. |
| 6,007,567 A | 12/1999 | Bonutti | 6,267,766 B1 | 7/2001 | Burkhart |
| 6,010,525 A | 1/2000 | Bonutti et al. | 6,269,716 B1 | 8/2001 | Amis |
| 6,016,727 A | 1/2000 | Morgan | 6,270,518 B1 | 8/2001 | Pedlick et al. |
| 6,022,352 A | 2/2000 | Vandewalle | 6,273,890 B1 | 8/2001 | Frazier |
| 6,022,373 A | 2/2000 | Li | 6,283,973 B1 | 9/2001 | Hubbard et al. |
| 6,024,758 A | 2/2000 | Thal | 6,283,996 B1 | 9/2001 | Chervitz et al. |
| 6,027,523 A | 2/2000 | Schmieding | 6,287,325 B1 | 9/2001 | Bonutti |
| 6,033,430 A | 3/2000 | Bonutti | 6,293,961 B2 | 9/2001 | Schwartz et al. |
| 6,039,753 A | 3/2000 | Meislin | 6,296,659 B1 | 10/2001 | Foerster |
| 6,042,601 A | 3/2000 | Smith | 6,299,615 B1 | 10/2001 | Huebner |
| 6,045,551 A | 4/2000 | Bonutti | 6,302,888 B1 | 10/2001 | Mellinger et al. |
| 6,045,573 A | 4/2000 | Wenstrom, Jr. et al. | 6,306,156 B1 | 10/2001 | Clark |
| 6,045,574 A | 4/2000 | Thal | 6,306,159 B1 | 10/2001 | Schwartz et al. |
| 6,048,343 A | 4/2000 | Mathis et al. | 6,309,405 B1 | 10/2001 | Bonutti |
| 6,051,006 A | 4/2000 | Shluzas et al. | 6,312,448 B1 | 11/2001 | Bonutti |
| 6,053,916 A | 4/2000 | Moore | 6,319,271 B1 | 11/2001 | Schwartz et al. |
| 6,056,752 A | 5/2000 | Roger et al. | 6,328,758 B1 | 12/2001 | Tornier et al. |
| 6,056,772 A | 5/2000 | Bonutti | 6,342,060 B1 | 1/2002 | Adams |
| 6,056,773 A | 5/2000 | Bonutti | 6,343,531 B2 | 2/2002 | Amis |
| 6,059,817 A | 5/2000 | Bonutti et al. | 6,364,897 B1 | 4/2002 | Bonutti |
| 6,062,344 A | 5/2000 | Okabe et al. | 6,368,322 B1 | 4/2002 | Luks et al. |
| 6,068,648 A | 5/2000 | Cole et al. | 6,368,326 B1 | 4/2002 | Dakin et al. |
| 6,074,403 A | 6/2000 | Nord | 6,368,343 B1 | 4/2002 | Bonutti et al. |
| 6,077,277 A | 6/2000 | Mollenauer et al. | 6,371,124 B1 | 4/2002 | Whelan |
| 6,077,292 A | 6/2000 | Bonutti | 6,379,361 B1 | 4/2002 | Beck, Jr. et al. |
| 6,086,591 A | 7/2000 | Bojarski | 6,383,199 B2 | 5/2002 | Carter et al. |
| 6,086,592 A | 7/2000 | Rosenberg et al. | 6,387,113 B1 | 5/2002 | Hawkins et al. |
| 6,086,608 A | 7/2000 | Ek et al. | 6,387,129 B1 | 5/2002 | Rieser et al. |
| 6,096,060 A | 8/2000 | Fitts et al. | 6,398,785 B2 | 6/2002 | Carchidi et al. |
| 6,099,530 A | 8/2000 | Simonian et al. | 6,409,743 B1 | 6/2002 | Fenton, Jr. |
| 6,099,568 A | 8/2000 | Simonian et al. | 6,413,260 B1 | 7/2002 | Berrevoets et al. |
| 6,117,160 A | 9/2000 | Bonutti | 6,423,088 B1 | 7/2002 | Fenton, Jr. |
| 6,117,162 A | 9/2000 | Schmieding et al. | 6,428,562 B2 | 8/2002 | Bonutti |
| 6,123,710 A | 9/2000 | Pinczewski et al. | 6,432,123 B2 | 8/2002 | Schwartz et al. |
| 6,132,433 A | 10/2000 | Whelan | 6,436,124 B1 | 8/2002 | Anderson et al. |
| 6,132,437 A | 10/2000 | Omurtag et al. | 6,440,134 B1 | 8/2002 | Zaccherotti et al. |

| | | |
|---|---|---|
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein et al. |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson et al. |
| 6,547,800 B2 | 4/2003 | Foerster et al. |
| 6,551,330 B1 | 4/2003 | Bain et al. |
| 6,551,343 B1 | 4/2003 | Tomala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tomala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,972,027 B2 * | 12/2005 | Fallin et al. ............... 606/232 |
| 6,980,903 B2 | 12/2005 | Daniels et al. |
| 6,986,781 B2 | 1/2006 | Smith |
| 6,989,034 B2 | 1/2006 | Hammer et al. |
| 7,066,944 B2 | 6/2006 | Laufer et al. |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,137,996 B2 | 11/2006 | Steiner et al. |
| 7,141,066 B2 | 11/2006 | Steiner et al. |
| 7,153,312 B1 | 12/2006 | Torrie et al. |
| 7,261,716 B2 | 8/2007 | Strobel et al. |

| | | |
|---|---|---|
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0019649 A1* | 2/2002 | Sikora et al. ............ 606/232 |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120292 A1 | 8/2002 | Morgan |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0169452 A1 | 11/2002 | Tormala et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078617 A1* | 4/2003 | Schwartz et al. ........... 606/230 |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1* | 7/2003 | Bojarski et al. ........... 606/228 |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0111117 A1 | 6/2004 | Colleran et al. |
| 2004/0122431 A1 | 6/2004 | Biedermann et al. |
| 2004/0138664 A1 | 7/2004 | Bowman |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0220574 A1 | 11/2004 | Pelo et al. |
| 2004/0225292 A1 | 11/2004 | Sasso et al. |
| 2004/0236353 A1 | 11/2004 | Bain et al. |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0064042 A1 | 3/2005 | Vunjak-Novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | McGuire et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0267479 A1 | 12/2005 | Morgan et al. |
| 2005/0277961 A1 | 12/2005 | Stone et al. |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0030948 A1 | 2/2006 | Manrique et al. |
| 2006/0036265 A1 | 2/2006 | Dant |
| 2006/0064126 A1 | 3/2006 | Fallin et al. |
| 2006/0069334 A1 | 3/2006 | Moskowitz |
| 2006/0100627 A1 | 5/2006 | Stone et al. |
| 2006/0121084 A1 | 6/2006 | Borden et al. |
| 2006/0135958 A1 | 6/2006 | Marissen et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0229671 A1 | 10/2006 | Steiner et al. |
| 2006/0247642 A1 | 11/2006 | Stone et al. |
| 2006/0271192 A1 | 11/2006 | Olsen et al. |
| 2006/0282085 A1 | 12/2006 | Stone et al. |
| 2006/0293709 A1 | 12/2006 | Bojarski et al. |
| 2007/0016305 A1 | 1/2007 | Chudik |
| 2007/0055255 A1 | 3/2007 | Siegel |
| 2007/0078435 A1 | 4/2007 | Stone et al. |
| 2007/0083236 A1 | 4/2007 | Sikora et al. |
| 2007/0185532 A1 | 8/2007 | Stone et al. |
| 2008/0027446 A1 | 1/2008 | Stone et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0255613 A1 | 10/2008 | Kaiser et al. |
| 2009/0082805 A1 | 3/2009 | Kaiser et al. |

FOREIGN PATENT DOCUMENTS

| | | |
|---|---|---|
| AU | 4402/66 | 10/1967 |

| | | |
|---|---|---|
| AU | 440266 | 10/1967 |
| AU | 22237/67 | 11/1968 |
| AU | 5028569 | 8/1970 |
| AU | 58504/69 | 1/1971 |
| AU | 59638/69 | 2/1971 |
| AU | 15054/70 | 11/1971 |
| AU | 36151/71 | 5/1973 |
| AU | 43812/68 | 9/1973 |
| AU | A-71108/87 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2 19 009 C2 | 11/1979 |
| DE | 3027138 | 12/1981 |
| DE | 3225620 A1 | 2/1983 |
| DE | 3136083 | 3/1983 |
| DE | 233 303 A1 | 2/1986 |
| DE | 4127550 | 2/1993 |
| DE | 4302397 | 7/1993 |
| EP | 0108912 A2 | 5/1984 |
| EP | 0 129 422 | 12/1984 |
| EP | 0129442 | 12/1984 |
| EP | 0172130 | 2/1986 |
| EP | 0 241 240 | 10/1987 |
| EP | 0241792 | 10/1987 |
| EP | 0260970 A2 | 3/1988 |
| EP | 0270704 | 6/1988 |
| EP | 0282789 | 9/1988 |
| EP | 0137406 | 5/1989 |
| EP | 0315371 A2 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0 415 915 | 3/1991 |
| EP | 0440991 | 8/1991 |
| EP | 0441065 | 8/1991 |
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 A2 | 5/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 A1 | 5/1999 |
| EP | 0913131 | 5/1999 |
| EP | 0995409 | 4/2000 |
| EP | 1013229 A2 | 6/2000 |
| EP | 1093773 | 4/2001 |
| EP | 1093774 | 4/2001 |
| EP | 1555945 | 7/2005 |
| FR | 2655840 | 6/1991 |
| FR | 2682867 | 4/1993 |
| FR | 2687911 | 9/1993 |
| FR | 2704140 | 10/1994 |
| FR | 2770764 | 5/1999 |
| GB | 401677 | 11/1933 |
| GB | 1413477 | 11/1975 |
| GB | 1485681 | 9/1977 |
| GB | 2 083 751 | 3/1982 |
| GB | 2 118 474 | 11/1983 |
| GB | 2227175 | 7/1990 |
| GB | 2253147 | 9/1992 |
| GB | 2312376 | 10/1997 |
| JP | 53-62911 | 5/1978 |
| JP | 53-62912 | 5/1978 |
| JP | 53-74942 | 6/1978 |
| JP | 53-78230 | 6/1978 |
| JP | 54-166092 | 11/1979 |
| JP | 54-166093 | 11/1979 |
| JP | 54-176284 | 12/1979 |
| JP | 54-178988 | 12/1979 |
| JP | 59-21775 | 2/1984 |
| JP | 62-159647 | 7/1987 |
| JP | 62-295657 | 12/1987 |
| JP | 5269160 | 10/1993 |
| JP | 5300917 | 11/1993 |
| JP | 751292 | 2/1995 |
| JP | 10211213 | 8/1998 |
| WO | WO83/00615 | 3/1983 |
| WO | WO 86/03666 | 7/1986 |
| WO | WO 87/01270 | 3/1987 |
| WO | WO-8901767 | 3/1989 |
| WO | WO-8909030 | 10/1989 |
| WO | WO 89/10096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO9822047 | 5/1998 |
| WO | WO-9822048 | 5/1998 |
| WO | WO9901084 | 1/1999 |
| WO | WO9912480 | 3/1999 |
| WO | WO-9944544 | 9/1999 |
| WO | WO-0040159 | 7/2000 |
| WO | WO 0139671 A1 | 6/2001 |
| WO | WO0139671 A1 | 6/2001 |
| WO | WO0236020 A1 | 5/2002 |
| WO | WO-03071962 | 9/2003 |
| WO | WO-03077772 | 9/2003 |
| WO | WO-2005104992 | 11/2005 |

OTHER PUBLICATIONS

Hecker AT, et al., "Pull-out strength of suture anchors for rotator cuff and Bankart lesion repairs," Am J Sports Med. 1993.

Flavia Namie Azato, et al. "Traction endurance biomechanical study of metallic suture anchors at different insertion angles," Acta ortop. bras., vol. 11, No. 1, Sao Paulo, Jan./Mar. 2003.

F. Alan Barber, M.D., "Uses and Abuses of Sutures and Anchors," ShoulderScope, San Diego Shoulder Arthroscopy Library.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

Opus Medical; The AutoCuff System; www.opusmedical.com.; 2003.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.

Roy Alan Majors, M.D.; "Meniscal repairs: proven techniques and current trends," Lippincott Williams & Wilkins, Inc.; 2002.

Shoulder Arthroscopy; pp. H-2-H-22.

Stuart E. Fromm, MD., "Surgical Technique for Repair of Meniscal Tears", published in RapidLoc Meniscal Repair Systems, Printed in the USA P/N 900564 Rev. A Feb. 2001.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

"EZ Loc Femoral Fixation Device," copyright 2005 Arthrotek, Inc. (8 sheets).

"Panalok Anchor with PDS II and Ethibond Suture", Mitek Products Ethicon, 1997.

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

Bio-Intrafix (TCP/PLA & Intrafix, Tibial Soft Tissue Fasteners, by DePuy Mitek, 6 sheets, (date unknown).

Lawhorn, M.D., Keith, MaxFire™ Meniscal Repair Device with Zip Loop™ Technology, Biomet Sports Medicine, Feb. 29, 2008.

Opus Medical; The AutoCuff System; www.opusmedical.com; 2003.

ToggleLoc™ Femoral Fixation Device, Arthrotek, Mar. 31, 2006.

US 6,238,418, 05/2001, Schwartz et al. (withdrawn)

* cited by examiner

METHOD AND APPARATUS FOR PERFORMING MENISCUS REPAIR

FIELD

This invention relates generally to a method and apparatus for use in repairing soft tissue, and more particularly, to a method and apparatus for repairing a torn meniscus during arthroscopic surgery.

BACKGROUND

There are many techniques employed to repair damaged soft tissue. These techniques include suturing, stapling, taping and the like. Selection of which technique to employ depends upon the type of soft tissue being repaired, the soft tissue location and the required strength of the repair. While there exists many techniques to repair soft tissue, there is a growing need to easily and quickly repair a torn meniscus in the knee during arthroscopic surgery.

The meniscus tissue is a fibrocartilaginous structure in the knee joint which performs multiple critical functions, including contributing to normal knee biomechanics and the general well-being of the joint. Generally, the menisci are comprised of two C-shaped fibrocartilaginous structures residing on the tibial plateau. The peripheral rim of a meniscus is thick, tapering to a thin, free inner border. The superior surface is concave to contact the femoral condyles, while the inferior surface is flat to contact the tibial plateau. The fibers forming the menisci are mainly oriented circumferentially throughout the meniscus, parallel to the peripheral border, to withstand hoop stresses placed upon the meniscus by the femoral condyles. It is generally recognized that repair of meniscal lesions, to the extent possible, is preferable to excision so as to attempt to maintain the normality of the meniscus and have it continue to function as intended.

One technique used to repair a torn meniscus is by means of suturing the tear by use of a suture and suture needle. One method of utilizing a suture and suture needle includes inserting the needles through the identified area and across the tear. Once the needles exit the knee joint they are pulled out and removed from the connected suture spanning between the needles. The suture is subsequently tied outside the tissue so that a horizontal suture extends in the meniscus. The process of tying the ends of a suture is time consuming and may result in an insufficient hold on the outside tissue.

Other techniques involve implanting surgical fasteners using an implanting device such as a spring gun. One disadvantage associated with utilizing a surgical fastener is the potential for the surgical fastener to migrate once it has been implanted which could potentially cause patient discomfort. Another disadvantage is that often only the tips of the fastener may be holding the tear together. What is needed then is a method and apparatus for repairing a torn meniscus which does not suffer from the above-mentioned disadvantages.

SUMMARY

A method of repairing a tear in body tissue includes inserting a needle containing a retaining head from a first insertion position on a first outer surface of the body tissue, through the tear and to a second outer surface of the body tissue. The retaining head is ejected from the insertion needle and grasps the second outer surface in an engaged position. An anchor coupled to the retaining head is advanced from a second insertion position on the first outer surface of the body tissue to a position at least through a portion of the tear. The anchor is coupled to the retaining head by a flexible member that extends a distance along the first outer surface of the body tissue from the first insertion position to the second insertion position.

According to other features, ejecting the retaining head from the insertion needle includes advancing a plunger within the needle toward a distal opening of the needle. The retaining head is deployed from the distal opening. The needle is removed from the body tissue at the first insertion position. Advancing the plunger includes guiding the flexible member along a longitudinal slot disposed along the needle. Advancing the anchor includes locating a distal end of a hollow tube on the second insertion position, the hollow tube containing the anchor therein. The plunger is advanced within the hollow tube a predetermined distance toward the distal end thereby advancing the anchor to a desired location.

An apparatus for repairing a tear in body tissue includes a retaining head for grasping a retaining surface of the body tissue and an anchor for being implanted at a position at least through a portion of the tear. A flexible member is coupled to and extends between the retaining head and the anchor. The flexible member includes an intermediate portion extending along an insertion surface of the body tissue.

According to other features, the anchor is disposed in the body tissue at a location between the tear and the retaining surface and passes through the tear. The flexible member urges the anchor toward the insertion surface of the body tissue and urges the insertion surface of the tissue toward the anchor thereby urging opposite sides of the tear to contact. The flexible member urges the retaining head toward the insertion surface of the body tissue and urges the insertion surface of the tissue toward the retaining head thereby urging opposite sides of the tear to contact.

Further areas of applicability of the present disclosure will become apparent from the detailed description provided hereinafter. It should be understood that the detailed description and various examples, while indicating various embodiments of the invention, are intended for purposes of illustration only and are not intended to limit the scope of the following claims.

BRIEF DESCRIPTION OF THE FIGURES

The present invention will become more fully understood from the detailed description and the accompanying drawings, wherein.

DETAILED DESCRIPTION OF VARIOUS EMBODIMENTS

The following description of various embodiment(s) is merely exemplary in nature and is in no way intended to limit the application or uses.

Figure 1A:
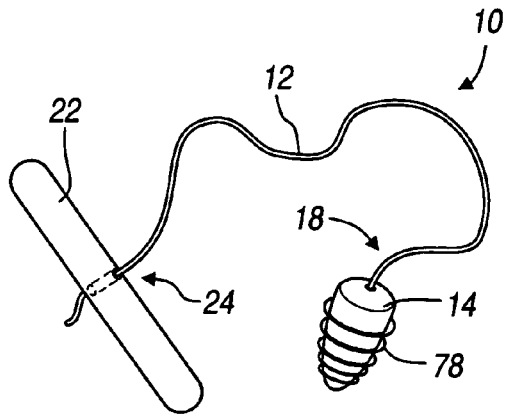
FIG. 1A is a perspective view of the meniscus repair apparatus according to the present teachings.

With initial reference to FIG. 1A, an apparatus for repairing a tear in meniscal tissue is shown generally at reference 10. The apparatus 10 includes a suture 12 extending between an anchor 14 disposed on a first end 18 and a retaining head 22 disposed on a second end 24.

Figure 1B:
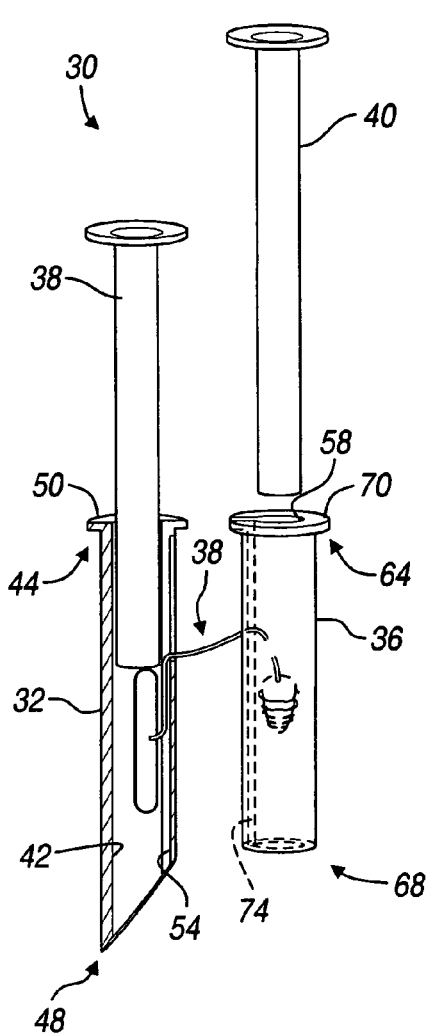
FIG. 1B is a front view of the implantation apparatus for use with the meniscus repair apparatus of FIG. 1A shown with the needle portion in section.

With continued reference to FIG. 1A and further reference to FIG. 1B, an insertion apparatus 30 for implanting the tissue repair apparatus 10 is shown. The insertion apparatus 30 generally includes a needle portion 32 and a hollow tube portion 36. Plungers 38 and 40 are slidably received within the respective needle portion 32 and the tube portion 36. The needle portion 32 is tubular and presents a longitudinal passage 42 extending between a proximal end 44 and a distal end 48 for receiving the plunger 38. The distal end 48 is shaped to pierce the body tissue during implantation as will be described in greater detail. The proximal end 44 has a collar 50 radially arranged to encourage gripping by the user. A slot 54 is longitudinally arranged between the distal and proximal end 44 and 48 for accommodating the suture 12 during implantation.

The hollow tube portion 36 presents a longitudinal passage 58 extending between a proximal end 64 and a distal end 68. The plunger 40 is slidably received within a passage 58. A collar 70 is arranged on the proximal end 64 for encouraging gripping by the user. A slot 74 extends between the proximal end 64 and the distal end 68 for accommodating the suture 12 during implantation.

With particular reference to FIG. 1A, the tissue repair apparatus 10 will now be described in greater detail. The anchor 14 includes retaining members 78 disposed thereon for gripping surrounding tissue in an implanted position. Although the retaining members 78 are represented as contoured radial rings, those skilled in the art will recognize that any alternate structure conducive of providing a gripping action may be employed such as barbs, threads and the like. The anchor 14 may be insert molded onto the suture 12 during assembly or attached in any other appropriate manner. The suture 12 may comprise through holes formed at intervals thereon to allow resin to incorporate between the suture 12 and the anchor 14 during molding to prevent slipping. The retaining head 22 is tied or otherwise secured to the opposite end 24 of the suture 12. The retaining head 22 resembles a T-shaped member and is formed of rigid material such as stainless steel, aluminum or polypropylene. As shown in FIG. 1B, the retaining head 22 is movable into a substantially parallel relationship with the suture 12 to cooperate with the longitudinal passage 42 of the needle member 32.

Figure 2:
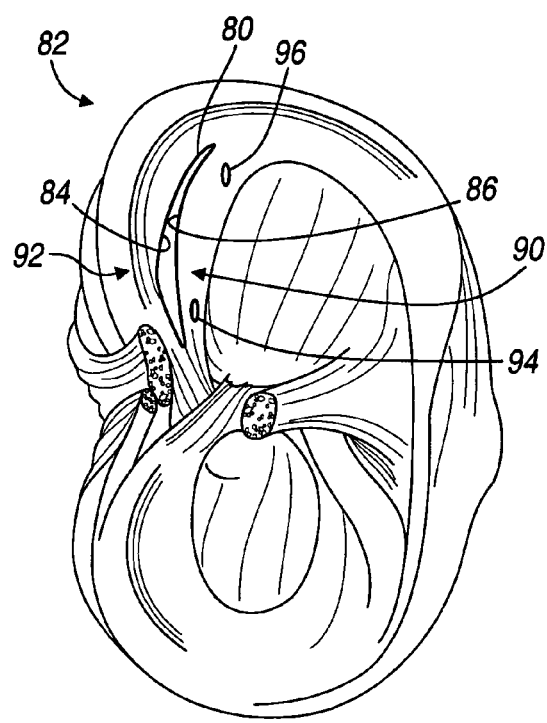
FIG. 2 is an environmental view of a human knee illustrating a tear in the meniscal tissue.
Figure 3:
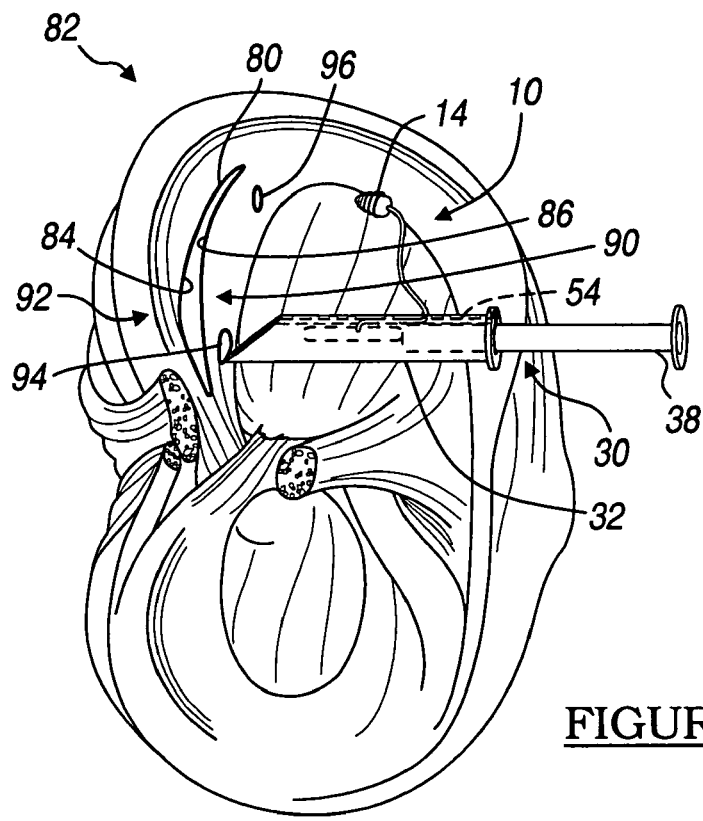
FIG. 3 is a perspective view of the needle portion of the insertion apparatus positioned at a first insertion position.

Turning now to FIG. 2, a human knee is shown having a tear 80 in the meniscus 82. The tear 80 is defined by a first and second side 84 and 86 and is positioned in the meniscus 82 for illustrative purposes. In this way, it is appreciated that the tear 80 may be located in an alternative location along the meniscus 82. The meniscus 82 has a first and second outer surface 90 and 92. The first surface 90 defines an insertion surface and the second surface 92 defines a retaining surface. A first insertion location 94 is identified on the second outer surface 92 as an exemplary location for penetrating the meniscal tissue 82 with the distal end 48 of the needle 32. Similarly, a second insertion location 96 is identified in an offset relationship from the first insertion location 94 for positioning the distal end 68 of the hollow tube 36 thereon.

FIGS. 3-7 illustrate the implantation of the tissue repair apparatus 10. With initial reference to FIGS. 3 and 4, insertion of the retaining head 22 will be described in greater detail. At the outset, the user positions the retaining head 22 within the longitudinal passage 42 of the needle 32. The suture 12 preferably lies proximate to the longitudinal slot 54 to allow the suture 12 to pass through if needed during assembly. At this time, the anchor 14, disposed on the opposite end 18 of the suture 12, may be free to move (FIG. 3), or alternatively, may be positioned within the hollow tube 36 (not shown). Once the first insertion position 94 is identified, the user penetrably advances the needle 32 from the insertion surface 92 through the tear 80 and to the retaining surface 90. As previously mentioned, the structure of the distal end 48 of the needle 32 is sharp to allow advancement through the meniscus 82.

Figure 4:
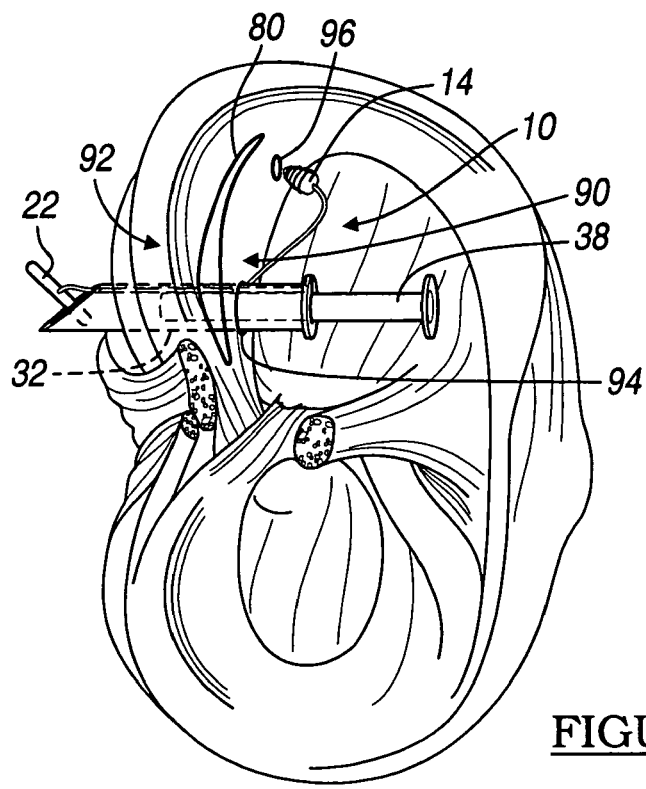
FIG. 4 is a perspective view of the needle portion shown advanced to an opposite outer surface of the meniscus prior to deployment of the retaining head.
Figure 5:
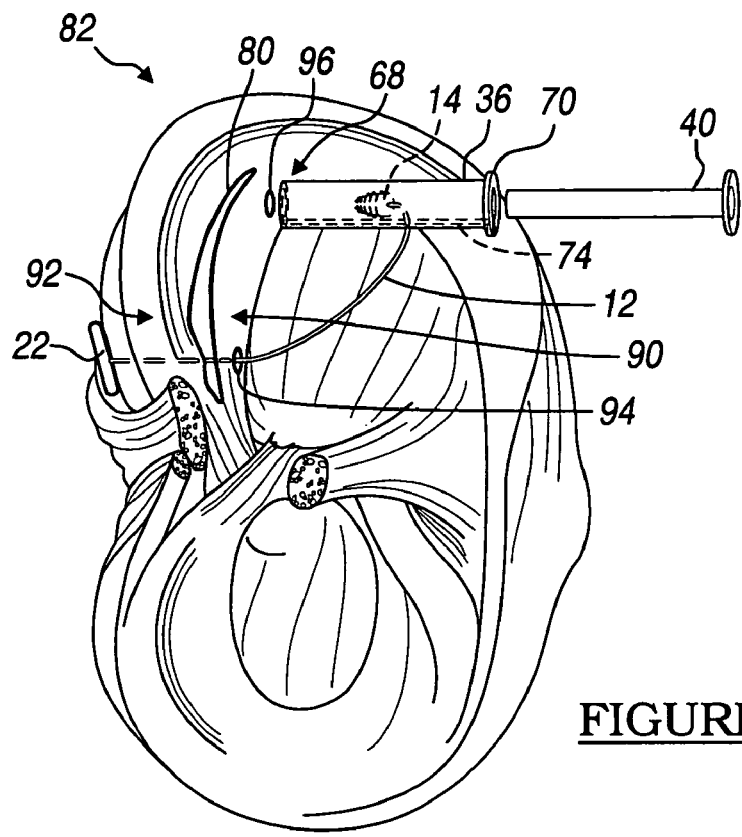
FIG. 5 is a perspective view of the hollow tube portion positioned at the second insertion position.

Next, the plunger 38 is advanced through the longitudinal passage 42 in the needle 32 to deploy the retaining head 22 (FIG. 4). The retaining head 22 moves from a parallel relationship with the suture 12 while within the needle 32 to a transverse relationship with the suture 12 upon deployment. The needle 32 and plunger 38 are subsequently removed from the meniscus 82 and the retaining head 22 is positioned in a flush relationship with the retaining surface 90 (FIG. 5)

Figure 6:
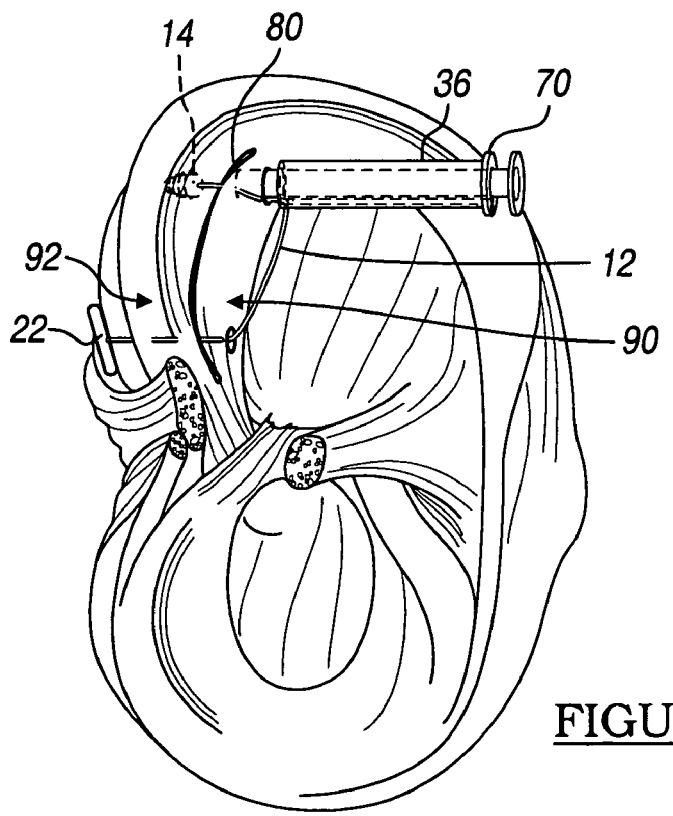
FIG. 6 is a perspective view of the hollow tube shown after advancing the anchor to a desired location.

Referencing now FIGS. 5-7, implantation of the anchor 14 will be described. The anchor 14 is placed into the hollow tube member 36. Preferably the suture 12 is aligned proximate to the slot 74 to allow the suture 12 to fall through the slot 74 during insertion if desired. The hollow tube 36 is placed onto the second insertion position 96. The second insertion position 96 is chosen to provide an adequate distance from the first insertion position 94 for the suture 12 to span across after implantation. The distance between the first and second insertion position 94 and 96 defines a force distribution distance whereby the suture 12 spans across. Accordingly, the user can choose a distance to distribute the force generated at the suture 12 into the insertion surface 92 by the retaining head 22 and anchor 14 once implanted.

After the distal end 68 of the hollow tube 36 is placed over the second insertion position 96, the plunger 40 is slidably advanced toward the distal end 68 of the tube 36. The plunger 40 subsequently passes the anchor 14 through at least a portion of the tear 80. As shown in FIG. 6, the anchor 14 is advanced to a location between the tear 80 and the retaining surface 90. Preferably, the anchor 14 is advanced to a location whereby any slack in the suture 12 is removed. During advancement of the anchor 14 into the meniscus 82, the suture 12 passes through the slot 74. As the slack is removed in the suture 14, the first side of the tear 84 is urged toward the second side 86 thereby closing the tear 80. The hollow tube 36 is then removed from the insertion surface 92.

Figure 7:
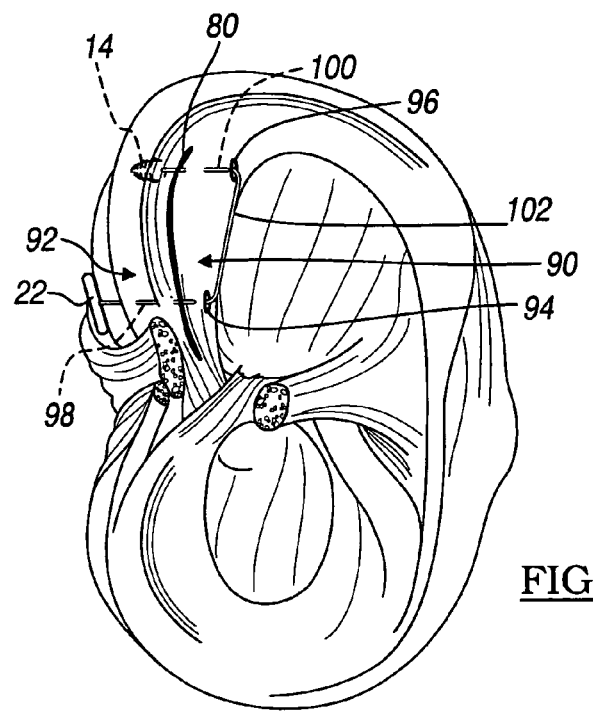
FIG. 7 illustrates the meniscus repair apparatus in an implanted position.

As shown in FIG. 7, the suture 12 defines a first portion 98, a second portion 100 and an intermediate portion 102 in an installed position. The first portion 98 extends from the retaining head 22 through the tear 80 and to the first insertion position 94. The second portion 100 extends from the anchor 14, through the tear 80 and to the second insertion position 96. The intermediate portion 102 extends along the insertion surface 92 between the first and second insertion position 94 and 96.

Figure 8:
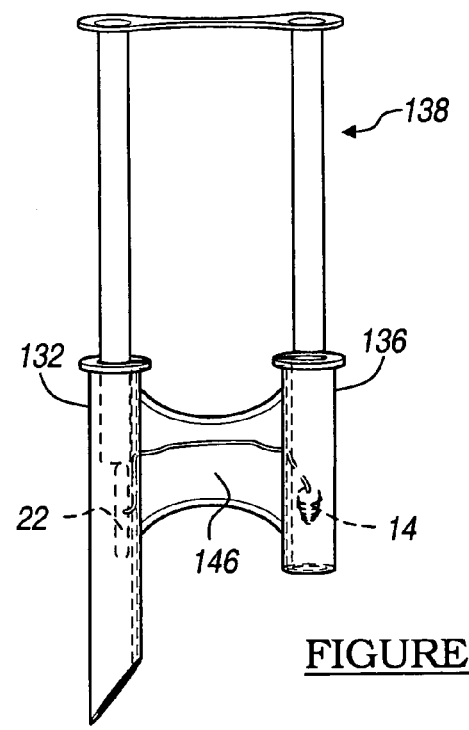
FIG. 8 illustrates an implantation apparatus according to a various embodiment.

According to various features, an insertion apparatus 130 is shown in FIG. 8. The insertion apparatus 130 employs similar features as the insertion apparatus 30 as previously described and will be identified with like reference numerals. The insertion apparatus provides a needle 132 and a hollow tube 136 arranged in a fixed relationship. The insertion apparatus 130 allows the user to implant the retaining head 22 and the anchor 14 simultaneously. The distance between the first and second insertion position 94 and 96 is fixed by the structure of a cross brace 146. As shown in FIG. 8, the cross brace 146 is integral to the needle 132 and hollow tube 136. However, a plurality of removably fixed cross braces 146 may be provided for controlling a fixed distance for multiple applications. It is appreciated that plunger mechanism 138 may comprise separate plungers for advancing the retaining head 22 and the anchor 14 sequentially.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. A method of repairing a tear in body tissue comprising:
   inserting a needle containing a retaining head therein from a first insertion position on a first outer surface of the body tissue, through the tear and to a second outer surface of the body tissue;
   ejecting said retaining head from said needle, said retaining head grasping said second outer surface in an engaged position; and
   locating a blunt end of a hollow tube adjacent to the body tissue without penetrating the body tissue at a second insertion position distinct from said first insertion position, said hollow tube containing an anchor therein; and
   advancing said anchor by advancing a plunger within said hollow tube toward said blunt end, said anchor piercing the body tissue ahead of said plunger and advancing to a position within the body tissue intermediate a portion of the tear and said second outer surface of the body tissue, said anchor coupled to said retaining head by a flexible member that extends from said first insertion position to said second insertion position, wherein a first terminal end of said flexible member is coupled to said retaining head and a second terminal end of said flexible member is coupled to said anchor.

2. The method of claim 1 wherein ejecting said retaining head from said needle comprises:
   advancing a plunger within said needle toward a distal opening of said needle;
   deploying said retaining head from said distal opening; and
   removing said needle from said body tissue at said first insertion position.

3. The method of claim 2 wherein said advancing said plunger within said needle further comprises:
   guiding said flexible member along a longitudinal slot disposed along said needle.

4. The method of claim 1 wherein said advancing said plunger further comprises:
   guiding said flexible member along a longitudinal slot disposed along said hollow tube.

5. The method of claim 1 wherein locating said blunt end of said hollow tube comprises:
   locating said blunt end of said hollow tube a predetermined offset distance from said first insertion position whereby said advancing said anchor to said position within the body tissue makes said flexible member taught between said first and second insertion positions.

6. The method of claim 1 wherein ejecting said retaining head and advancing said anchor are simultaneously performed.

7. The method of claim 1, further comprising simultaneously piercing the body tissue with said needle and locating said blunt end adjacent to the body tissue.

8. The method of claim 1, further comprising fixing said needle relative to said hollow tube.

9. A method of repairing a tear in body tissue comprising:
   passing a needle from a first portion of the body tissue, through the tear and to an outer surface of the body tissue;
   ejecting a retaining head from said needle such that said retaining head lies against said outer surface in an engaged position;
   locating a blunt hollow member against said first portion of the body tissue without penetrating the body tissue; and
   deploying an anchor from said blunt hollow member, said anchor coupled to said retaining head by a flexible member, said anchor being advanced from said first portion, through the tear to a desired location within the body tissue intermediate the tear and said outer surface of the body tissue, wherein said flexible member extends a distance along said first portion of the body tissue and wherein a first terminal end of said flexible member is coupled to said retaining head and a second terminal end of said flexible member is coupled to said anchor.

10. The method of claim 9 wherein deploying said anchor to said desired location comprises:
    securing said first terminal end of said flexible member at only one location to said retaining head;
    molding said second terminal end of said flexible member to said anchor; and
    inserting said anchor to said desired location wherein said flexible member is taught between said anchor and said retaining head.

11. The method of claim 9 wherein ejecting said retaining head from said needle comprises:
    advancing a plunger within said needle toward a distal opening of said needle;
    deploying said retaining head from said distal opening; and
    removing said needle from said body tissue.

12. The method of claim 11 wherein advancing said plunger further comprises:
    guiding said flexible member along a longitudinal slot disposed along said needle.

13. The method of claim 11 wherein deploying said anchor comprises:
    locating a distal end of said blunt hollow member onto the body tissue, said blunt hollow member containing said anchor therein; and
    advancing a plunger within said blunt hollow member a predetermined distance thereby advancing said anchor to said desired location.

14. The method of claim 13 wherein the body tissue is a meniscus and the tear is a tear in the meniscus;
    wherein said first portion of the body tissue is a first outer surface of the meniscus;
    wherein said outer surface of the body tissue is a second outer surface of the meniscus; and
    wherein the desired location is in the meniscus.

15. A method of repairing a tear in a meniscus comprising:
    inserting a cannulated piercing member having a piercing end and defining a first length, said cannulated piercing member containing a retaining head therein from a first insertion position on a first outer surface of the meniscus, through the tear and to a second outer surface of the meniscus, said retaining head having a longitudinal body and positioned generally longitudinally within said cannulation;

ejecting said retaining head from said piercing member such that said retaining head engages said second outer surface of the meniscus; and positioning a terminal end of a hollow tube on said first outer surface; and advancing an anchor from said hollow tube, while said hollow tube remains external to said first out surface, said anchor being coupled to said retaining head, wherein said anchor is advanced from a second insertion position on said first outer surface of the meniscus to an implanted position, wherein in said implanted position, said anchor passes through a portion of the tear and remains within tissue defining the meniscus, said anchor coupled to said retaining head by a flexible member that extends a distance along said first outer surface of the meniscus, wherein a first terminal end of said flexible member is coupled to said retaining head and a second terminal end of said flexible member is coupled to said anchor.

16. The method of claim 15 wherein ejecting said retaining head from said piercing member comprises:

advancing a plunger within said piercing member toward a distal opening of said piercing member;

deploying said retaining head from said distal opening; and removing said piercing member from said meniscus at said first insertion position.

17. The method of claim 16 wherein advancing a plunger further comprises:

guiding said flexible member along a longitudinal slot disposed along said piercing member.

18. The method of claim 15 wherein advancing said anchor comprises:

locating a blunt end of said hollow tube on said second insertion position without penetrating the meniscus, said hollow tube containing said anchor therein, said hollow tube having a second length that is less than said first length, such that said piercing end extends beyond said blunt end; and advancing a plunger within said hollow tube a predetermined distance toward said distal end thereby advancing said anchor to a desired location in the meniscus, said anchor piercing the meniscus during said advancing.

19. The method of claim 18 wherein locating a blunt end of a hollow tube comprises:

locating said blunt end of said hollow tube a predetermined offset distance from said first insertion position whereby advancing said anchor to said desired location makes said flexible member taught between said first and second insertion positions to substantially close the tear.

20. The method of claim 18 wherein said cannulated piercing member and said hollow tube are distinct components fixedly coupled such that ejecting said retaining head and advancing said anchor are simultaneously performed, and inserting said cannulated piercing member and locating said blunt end are simultaneously performed.

21. A method of repairing a tear in body tissue comprising:

providing a plunger mechanism having a cannulated needle fixedly coupled to a hollow tube at a generally laterally offset relationship;

locating a retaining head into the cannulated needle and an anchor into the hollow tube, wherein terminal ends of a flexible member are connected to the retaining head and the anchor respectively;

locating the plunger mechanism relative to the body tissue such that a distal tip of the needle passes through a first insertion position of the body tissue, through the tear and to an outer surface of the body tissue, wherein a blunt end of the hollow tube concurrently locates adjacent to the body tissue without penetrating the body tissue at a second insertion position that is offset relative to the first insertion position; and concurrently advancing a first plunger through the cannulated needle and a second plunger through the hollow tube wherein the retaining head is ejected from the cannulated needle such that the retaining head lies against the outer surface of the body tissue and the anchor passes through the tear to a desired location within the body tissue intermediate the tear and the outer surface of the body tissue, the anchor directly engaging the body tissue upon deployment from the blunt end of the hollow tube, wherein the flexible member advances through respective slots formed along the cannulated needle and hollow tube during the concurrent advancement.

22. The method of claim 21, further comprising fixing the needle and the hollow tube substantially parallel to one another.

23. The method of claim 21, further comprising fixing the first plunger relative to the second plunger.

\* \* \* \* \*